United States Patent [19]
Kikuchi et al.

[11] Patent Number: 5,380,287
[45] Date of Patent: Jan. 10, 1995

[54] MEDICAL SOLUTION DELIVERY SYSTEM

[75] Inventors: Toshihiro Kikuchi, Suita; Hitoshi Futagawa, Kusatsu, both of Japan

[73] Assignee: Nissho Corporation, Osaka, Japan

[21] Appl. No.: 97,051

[22] Filed: Jul. 27, 1993

[30] Foreign Application Priority Data

Jul. 31, 1992 [JP] Japan .................. 4-225252

[51] Int. Cl.6 ............................ A61M 5/20
[52] U.S. Cl. ......................... 604/135; 604/152
[58] Field of Search ............ 604/135, 154, 155, 152

[56] References Cited

U.S. PATENT DOCUMENTS

| | | | |
|---|---|---|---|
| 2,725,877 | 12/1955 | Reiter et al. | 604/135 |
| 3,895,631 | 7/1975 | Buckles et al. | |
| 4,298,000 | 11/1981 | Thill et al. | 604/135 |
| 4,318,400 | 3/1982 | Peery et al. | |
| 4,381,006 | 4/1983 | Genese | |
| 4,597,754 | 7/1986 | Thill et al. | 604/135 |
| 4,681,566 | 7/1987 | Fenton, Jr. et al. | 604/135 |
| 4,755,172 | 7/1988 | Baldwin | 604/135 |
| 4,863,429 | 9/1989 | Baldwin | 604/135 |
| 5,037,306 | 8/1991 | Van Schoonhoven | 604/135 |
| 5,078,679 | 1/1992 | Reese | 604/135 |
| 5,080,652 | 1/1992 | Sancoff et al. | 604/132 |
| 5,105,983 | 4/1992 | Sancoff et al. | 222/103 |
| 5,147,311 | 9/1992 | Pickhard | 604/135 |
| 5,178,609 | 1/1993 | Ishikawa | 604/135 |

Primary Examiner—John G. Weiss

[57] ABSTRACT

A medical solution delivery system comprises a cylindrical container having an opening at one end and a port for a medical solution at the opposite end; a plunger slidably arranged in the container; a plunger-driving device for forcing the plunger to move towards the port of the container to deliver a medical solution therethrough; a capsule for holding the container, the plunger and the plunger-driving device; and a flow control device connected to the port of the container to control a flow rate of the solution delivered therefrom. The solution in the container is delivered through a flow control device connected to the port of the container.

7 Claims, 8 Drawing Sheets

MEDICAL SOLUTION DELIVERY SYSTEM

BACKGROUND OF THE INVENTION

1. Field of the Invention

The present invention relates to a medical solution delivery system and, more particularly, a system suitable for continuously delivering a medical solution to a blood vessel, extraduramater, subcutaneous tissue, or the bladder of a patient at a well-controlled flow rate.

2. Description of the Prior Art

In order to administer a very small amount of a medical solution such as a antibiotic agent, or carcinostatic agent, or the like to the blood vessel, bladder, or the like of a patient, there have been proposed various kinds of medical solution delivery systems comprising an expanded balloon of an elastic material with a medical solution filled therein, a housing for holding the balloon therein, and a flow control means connected to the balloon to control a flow rate of the solution, as disclosed in JP-A- S50-108790, JP-A- S56-102252, JP-A- H1-135360 and JP-A- H3-170163. In such a system, the medical solution is delivered from the balloon little by little by means of shrinkage thereof. In other words, the balloon is used as a container for storing a medical solution and as a motive power source for delivering the solution therefrom.

Accordingly, it is inevitable with such a medical solution delivery system to avoid influences of a material used for production of the balloon. The balloon is made of an elastomeric gum rubber, the force applied to the medical solution varies with time during injection, thus making it impossible to delivery the medical solution at the accurately controlled flow rate. In addition, it is required to use an elastomeric gum rubber having no problem caused by eluants.

SUMMARY OF THE INVENTION

It is therefore an object of the present invention to provide an inexpensive medical solution delivery system which enables delivery of a medical solution at a well-controlled flow rate over a wide range.

Another object of the present invention is to provide an infusion fluid delivery system which is simple in structure, easy to operate, and small in the number of components, and which has no fear of elution of chemical substances from the container.

According to the present invention, a medical solution delivery system comprising: (a) a cylindrical container having an opening at one end and a port for a medical solution at the opposite end; (b) a plunger slidably arranged in said container; (c) a plunger-driving means for forcing the plunger to move toward the port of the container to deliver a medical solution therethrough; (d) a capsule for holding the container, the plunger and the plunger-driving means; and (e) a flow control means connected to the port of the container to control a flow rate of the solution delivered therefrom.

As a motive power source for the plunger-driving means, constant force springs, rubber strings, coil springs and the like may be used, for example.

To make the medical solution delivery system ready for use, a medical solution, for example, an infusion fluid, is firstly drawn into the plunger device consisting of the cylindrical container and the plunger in the same manner as a well-known syringe. Then, the plunger device is arranged in the capsule so that the plunger is brought into contact with the plunger-driving means. The plunger is then forced to move towards the forward end of the container to remove all the air present in the system. After piercing the catheter into a vein of a patient, the plunger is further forced to move towards the forward end of the container so that the solution is delivered from the container at a flow rate controlled by the flow control means.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The above and other objects, features and advantages of the present invention will become apparent from the following description taken in conjunction with the preferred embodiments thereof with reference to the accompanying drawings which are given by way of illustration only, and thus are not limitative of the present invention, and wherein.

DETAILED DESCRIPTION OF THE PREFERRED EMBODIMENTS

Figure 1:
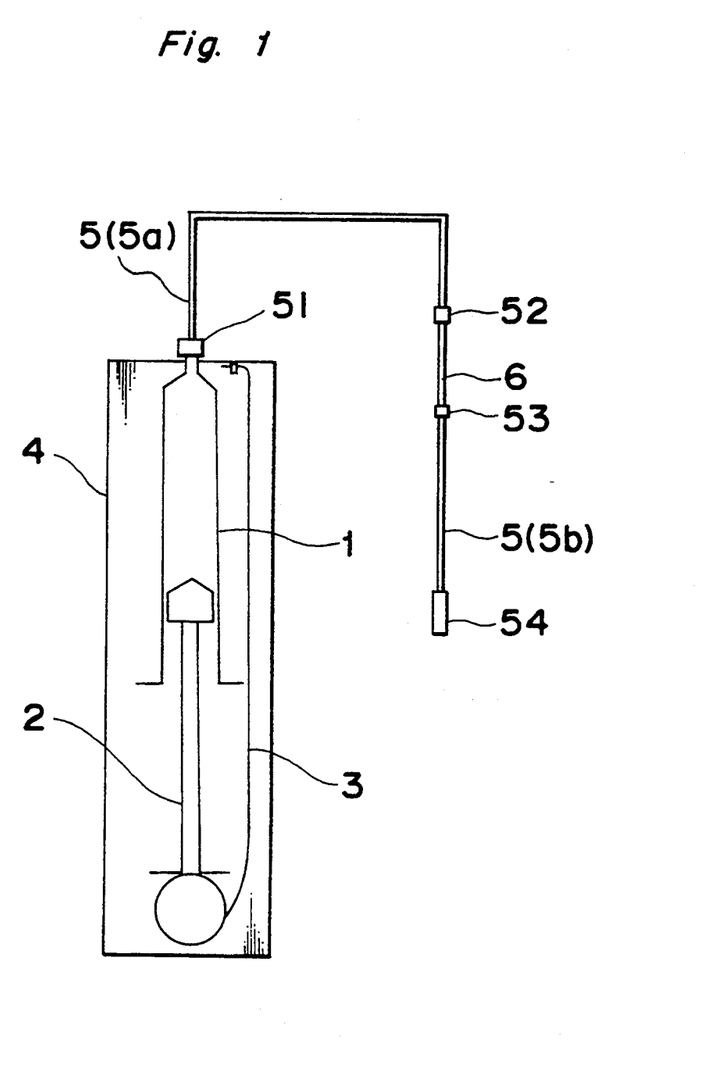
FIG. 1 is a schematic view of a medical solution delivery system illustrating one embodiment of the present invention.
Figure 2:
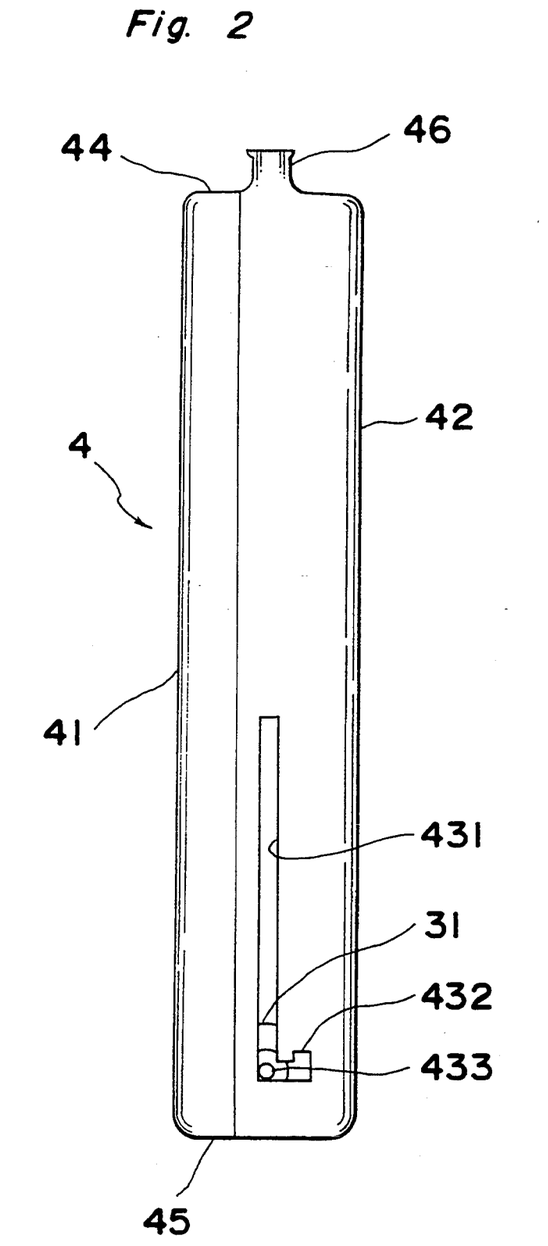
FIG. 2 is a front view of the medical solution delivery system of FIG. 1.
Figure 3:
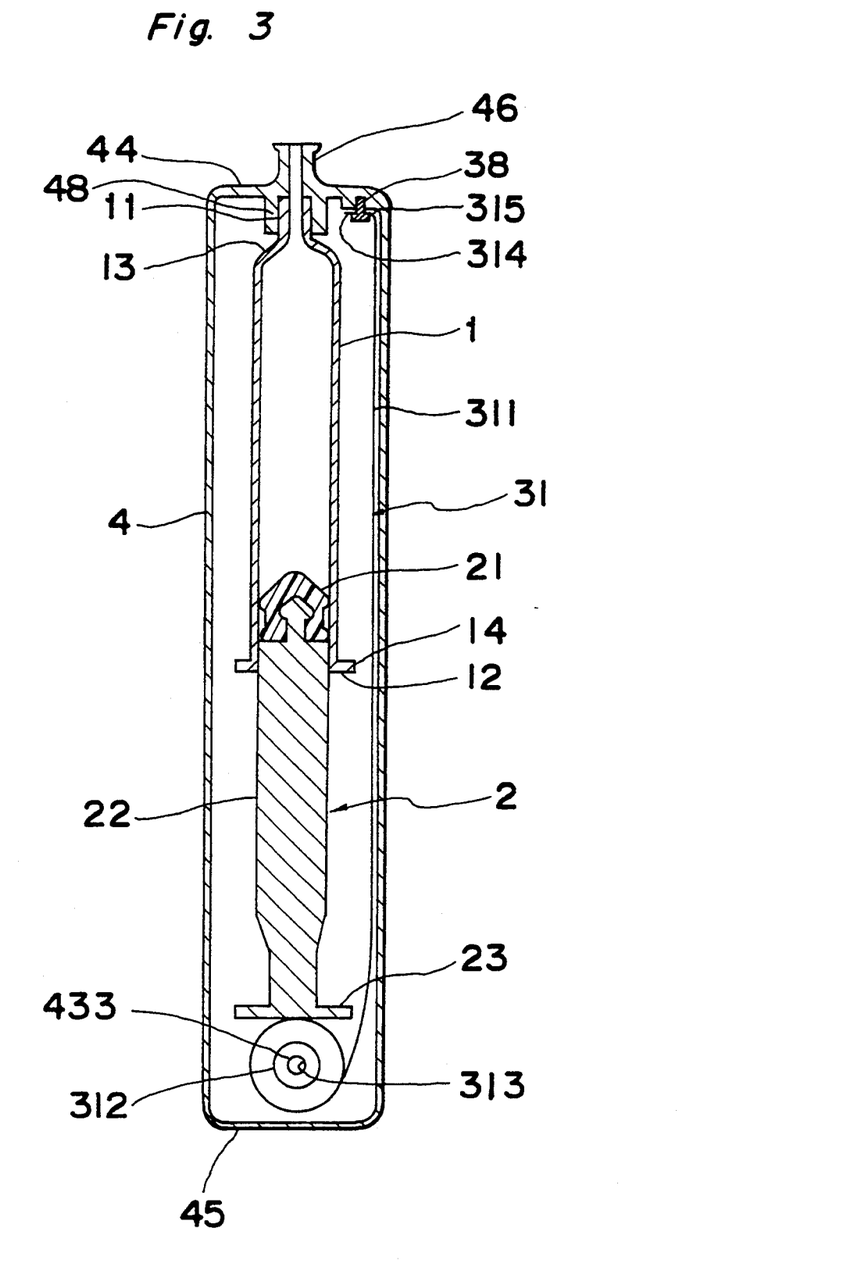
FIG. 3 is a vertical cross sectional view of the medical solution delivery system of FIG. 2.

Referring now to FIGS. 1 to 3, there is shown a medical solution delivery system embodying the present invention, which comprises a cylindrical container 1, a plunger 2 slidably arranged therein, a plunger-driving means 3 for forcing the plunger 2 to move smoothly within the container 1 towards the front end thereof, a capsule 4 for holding these components therein, and a connecting tube 5 provided with a flow control means 6 arranged therein to control a flow rate of a medical solution.

The container 1 is a cylindrical receptacle, usually made of glass or transparent synthetic resins such as polypropylene, polyester, poly(4-methylpentene-1), polycarbonate, and the like, having an open end 12 and a closed end 13 having a port 11.

The plunger 2 comprises a plunger rod 22 and a gasket 21 mounted on a front end thereof. The plunger rod 22 is usually made of glass or a synthetic resin such as polypropylene, polyethylene, polyester, polycarbonate, or the like. The plunger rod 22 has a flange 23 formed on the rear end thereof as an integral part thereof. The gasket 21 is usually made of butyl rubber or an olefin elastomer and used to seal a contacting area between the plunger 2 and cylindrical container 1 against leakage.

The above container 1 and the plunger 2 combined therewith constitute a syringe or a plunger device for draw injecting or withdrawing medical solutions, similar to a well-known syringe. Thus, the plunger device in this embodiment may be replaced with a commercially available syringe.

The capsule 4 is a cylindrical receptacle, usually made of a transparent material similar to that of the cylindrical container 1, having a closed end 45 at one end thereof and a narrow part 46 at the opposite end. As shown in FIG. 2, the capsule 4 is divided into two parts, i.e., a body 42 and a covering member 41, along a parting line parallel to an axis of the capsule 4 but spaced therefrom. The covering member 41 is removably attached to the capsule body 42 by fitting it in the latter, but the former may be hinged to the latter.

The capsule body 42 is provided with an L-shaped slit 431 extending from a middle part thereof along the barrel of the capsule body 42 to the rear part and then circumferentially extending therefrom to form a short arm portion with a cut 432.

The body 42 of the capsule 4 is provided with a cylindrical projection 48 for engagement with the container 1. This projection 48 extends inwardly from an inside wall of the front end 44 of the capsule 4 and is communicated with the narrow part 46 to allow the container 1 to communicate with the connecting tube 5 through the narrow part 11 thereof and the narrow part 46 of the capsule.

The plunger-driving means 3 comprises a constant force spring 31, such as CONSTON (Trademark of Sanko Hatsujo corporation). The spring 31 is wound around a drum 312 at one end thereof and at the opposite end 314 fixed to an inside wall of the front end 44 of the capsule 4 by means of a screw 38. To this end, the opposite end, i.e., front end of the spring 31 is bent at 314 and provided with a hole 315 through which the screw 38 is engaged with the threaded bore formed in the inside wall of the front end 44 of the capsule 4.

The drum 312 is provided with a rod 433 constituting an operating means. The rod 433 is slidably arranged in the L-shaped guide slit 431 of the capsule body 42 and adapted to be kept in the cut 432 before use. The wound part of the constant force spring 31 comes into contact with the flanged rear end of the plunger 2 when the rod 433 is released from the cut 432.

The connecting tube 5 is separated into two parts, i.e., 5a and 5b by means of the flow control means 6. The connecting tube 5a is connected at one end thereof to the cylindrical container 1 by a connector 51 and at the opposite end to one end of the flow control means 6 by a connector 52, whereas the connecting tube 5b is connected at one end thereof to the opposite end of the flow control means 6 by a connector 53 and at the other end to a connector 54 used for attachment of a catheter (not illustrated in the drawings). However, the connecting tube 5 is unnecessarily required for the delivery system of the present invention.

The flow control means 6 may have any configuration depending on the time required for administration of a drug or an amount of a drug per unit time. Examples of preferred flow control means are those comprising a narrow tube provided with a very small bore as disclosed in Japanese patents JP-A-64-70069 or JP-A-H1-135359, or those comprising a pipe with a very small diameter as disclosed in Japanese patent specifications JP-A- 2-11159 or JP-A- 3-140163.

To make the above medical solution delivery system ready for use, the rod 433 removably fitted in the bore 313 of the drum 312 is moved manually toward the rear end 45 of the capsule 4 along the guide slit 431 and the axis of the capsule 4 until it reaches to the corner of the slit 431 as shown in FIG. 2, and then displaced laterally from the axis of the capsule 4 to engage it with the cut 432 of the L-shaped slit 431.

Separate from the above, a medical solution to be transfused into a blood vessel of a patient is drawn into the plunger device composed of the cylindrical container 1 and the plunger 2 in the same manner as that of the well-known syringe and then the plunger device is set in the capsule 4, as shown in FIG. 3. Before of after setting the plunger device in the capsule 4, the tube 5 is connected to the narrow part 46 of the capsule 4 at one end thereof and to a catheter at the opposite end by the connector 54. In this case, the connecting tube 5 has been closed by a suitable closing means such as a clamp (not illustrated in the drawings).

After this, the closing means is removed from the tube to make a fluid communication between the cylindrical container and the catheter, and then the rod 433 is released from the cut 432. For this reason, the wound part of the constant force spring 31 comes into contact with the flanged rear end of the plunger 2 and the plunger 2 is applied with a constant force by the constant force spring 31 so that it is forced to move towards the front end of the cylindrical container 1 until the rod 433 reaches the front end of the guide slit 431. During movement of the plunger 2, all the air present in the container 1, the tube 5 and the catheter is expelled therefrom by the medical solution.

After the air is removed from the deliver system, the tube 5 or the catheter is clamped by the clamping means. Then, the catheter is inserted into the blood vessel of a patient and the rod 433 is pulled out from the bore 313 of the drum 312. Then, the clamping means is removed from the tube 5 or the catheter, and the plunger 2 is forced again by the constant force spring 31 to move towards the front end of the container 1 so that the medical solution in the container 1 is delivered therefrom through the port 11 and then injected into the blood vessel at the flow rate controlled by the flow control means 6.

Figure 5:
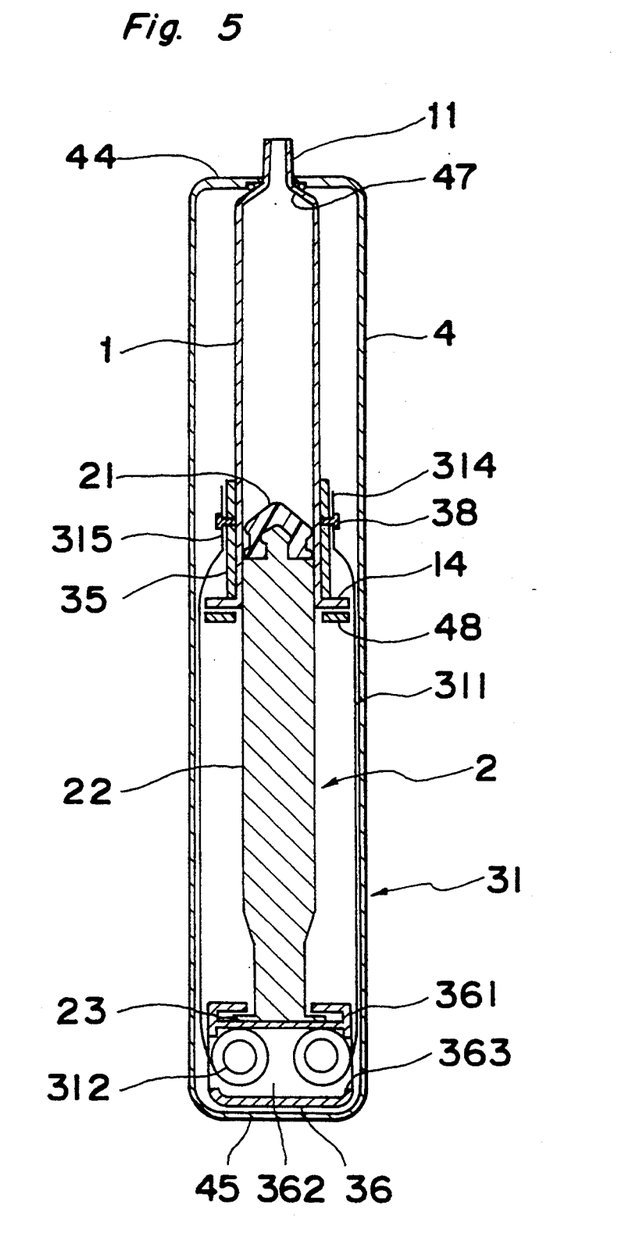
FIG. 5 is a cross sectional view of the medical solution delivery system, taken along a line X—X in FIG. 4.

In the embodiment of FIG. 1, the container 1 is provided with a flange 14 such as a hypodermic syringe, but there is no need to provide such a flange 14 on the open end of the container body 1, except for the case that the rear end of the cylindrical container is used for attachment of a free end of the plunger-driving means such as a constant force spring 31, as shown in FIG. 5.

Figure 4:
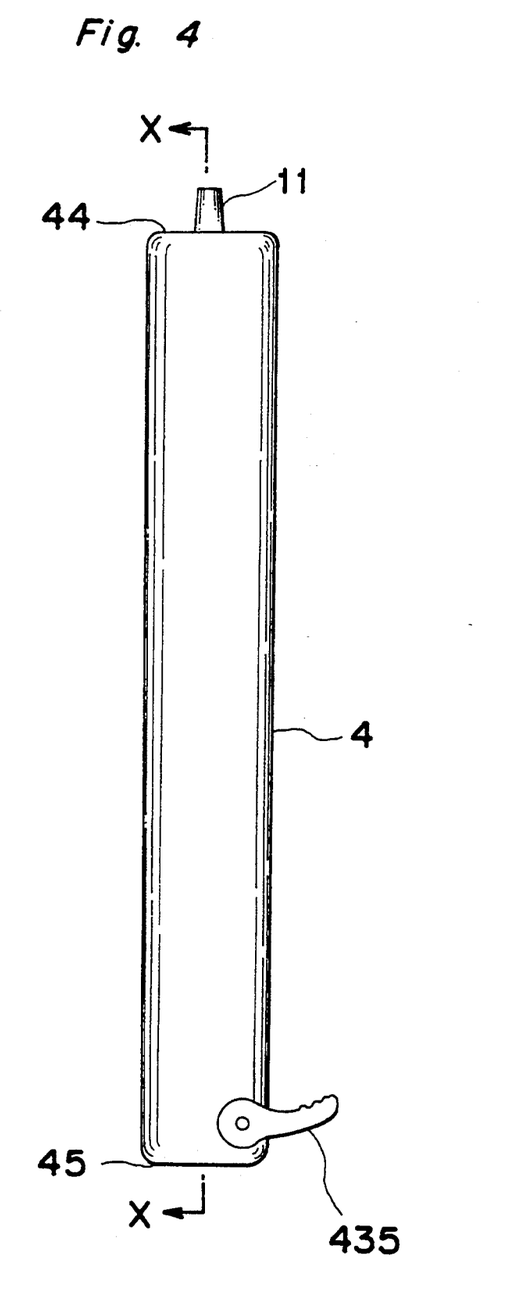
FIG. 4 is a front view of a medical solution delivery system illustrating another embodiment of the present invention.

Referring now to FIGS. 4 and 5, there is shown a modified form of a medical solution delivery system of the present invention. The medical solution delivery system in this embodiment comprises a syringe consisting of a cylindrical container 1 and a plunger 2 slidably arranged therein; a plunger-driving means 3 for forcing the plunger 2 to move smoothly within the cylindrical container 1 towards the front end thereof; and an inseparable capsule 4 having a chamber for holding the syringe and a plunger-driving means 3.

In this embodiment, the capsule 4 is composed of an inseparable cylindrical member and is provided at a front end thereof with a hole 47, through which a port or narrow part 11 of the cylindrical container 1 is protruded outwardly from the capsule 4, as shown in FIG. 5.

The plunger-driving means 3 comprises a pair of constant force springs 31, each of which is wound around a drum 312 at one end thereof and fixed to a cylindrical fixing member 35 at the opposite end 314 by means of a screw 38. The fixing member 35 is mounted on the cylindrical container 1. The wound part of the constant force springs 31 are held in a drum housing 36 fixed to the flange 23 of the plunger 2. The drum housing 36 is provided with a pair of slits 363 though which a leading part 311 of each spring 311 is stretched out to fix it to the fixing member 35.

The capsule 4 is provided at a rear part thereof with a lever 435 so that the spring 31 can be displaced from the outside of the capsule 4. The lever 435 is adapted to be engaged with the drum housing 36 to hold it in place during storage. In this case, the drums 312 are redoubtably mounted on the drum housing 36 by means of a shaft thereof. Thus, there is no need to provide an L-shaped guide slit in the capsule 4.

In use, the drum housing 36 is released from the lever 435 by turning it clockwise or counterclockwise after the delivery system is connected to a catheter through the tube 5 similar to that of FIG. 1. The plunger 2 is forced to move towards the front end of the cylindrical container 1 by means of the constant force springs 31 and the medical solution previously filled in the container 1 is injected into the blood vessel of a patient in the same manner as that in the embodiment of FIG. 1.

Figure 6:
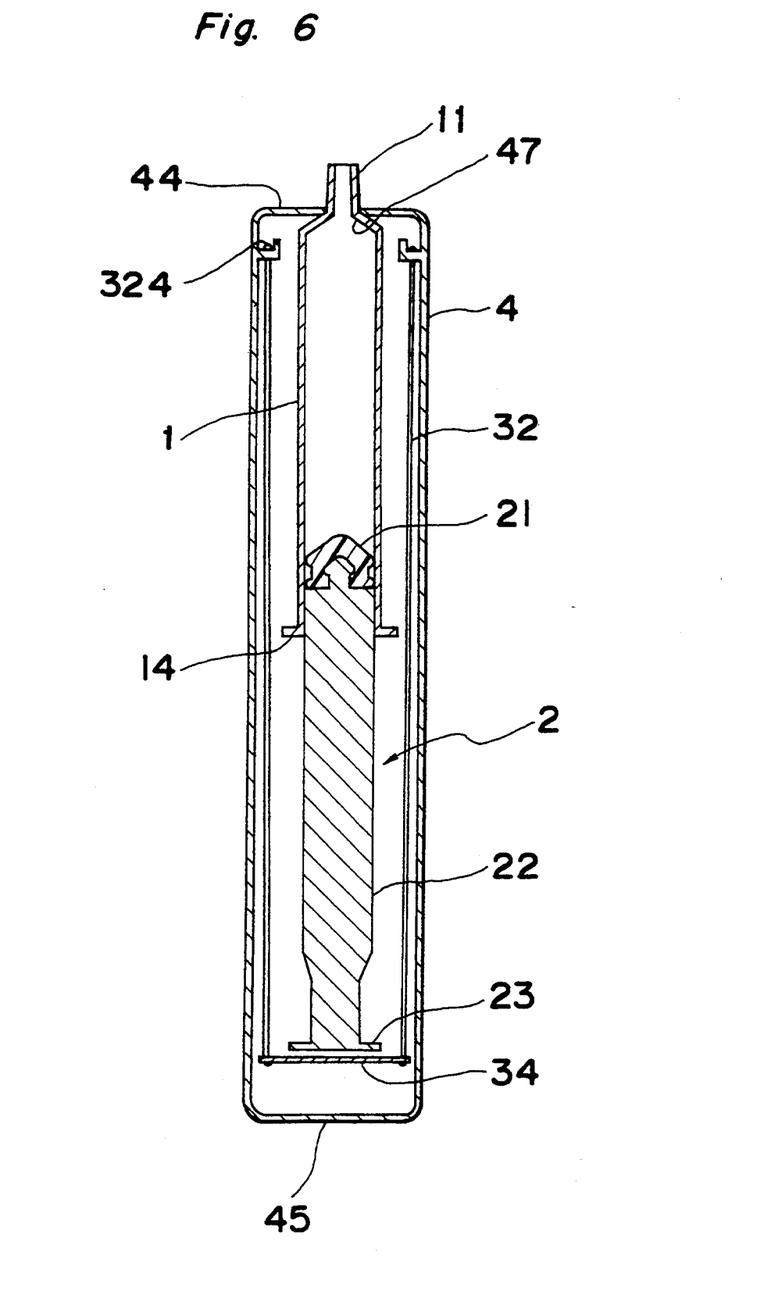
FIG. 6 is a sectional view of a medical solution delivery system illustrating still another embodiment of the present invention.

FIG. 6 shows another embodiment of a medical solution delivery system of the present invention. In this embodiment, the plunger-driving means 3 comprises two or more rubber strings 32 in the form of a wire, which are arranged at a regular distance around a syringe composed of a cylindrical container 1 and a plunger 2 and housed in a capsule 4. The spring wire 32, usually made of natural rubber or a synthetic rubber such as isoprene rubber, butadiene rubber, is fixed at one end 324 thereof to a rib on the side of the front part 44 of the capsule 4 and at the opposite end to a disk 34 which is adapted to come into contact with the flange 23 of the plunger 22.

To make this delivery system ready for use, the disk 34 is moved manually toward the rear end 45 of the capsule 4 and then the syringe charged with a medical solution is set in the capsule 4 so that the flange 32 comes into contact with the disk 34. In this embodiment, it is therefore required to use a separable capsule similar to that used in the embodiment of FIGS. 1 to 3.

As might be expected, the capsule 4 used in the above embodiment may be provided with a spring-operating means similar to that used in the embodiment of FIGS. 2 and 3. In this case, it is possible to use an inseparable capsule instead of the separable capsule 4.

Figure 7:
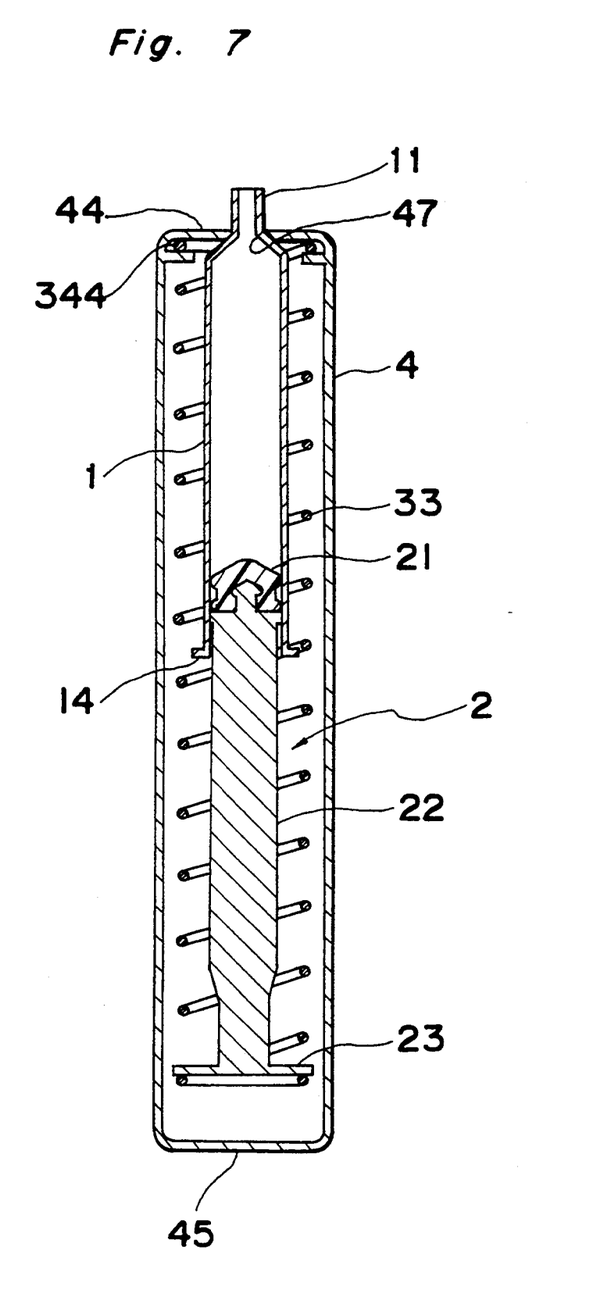
FIG. 7 is a sectional view of a medical solution delivery system illustrating still another embodiment of the present invention.
Figure 8:
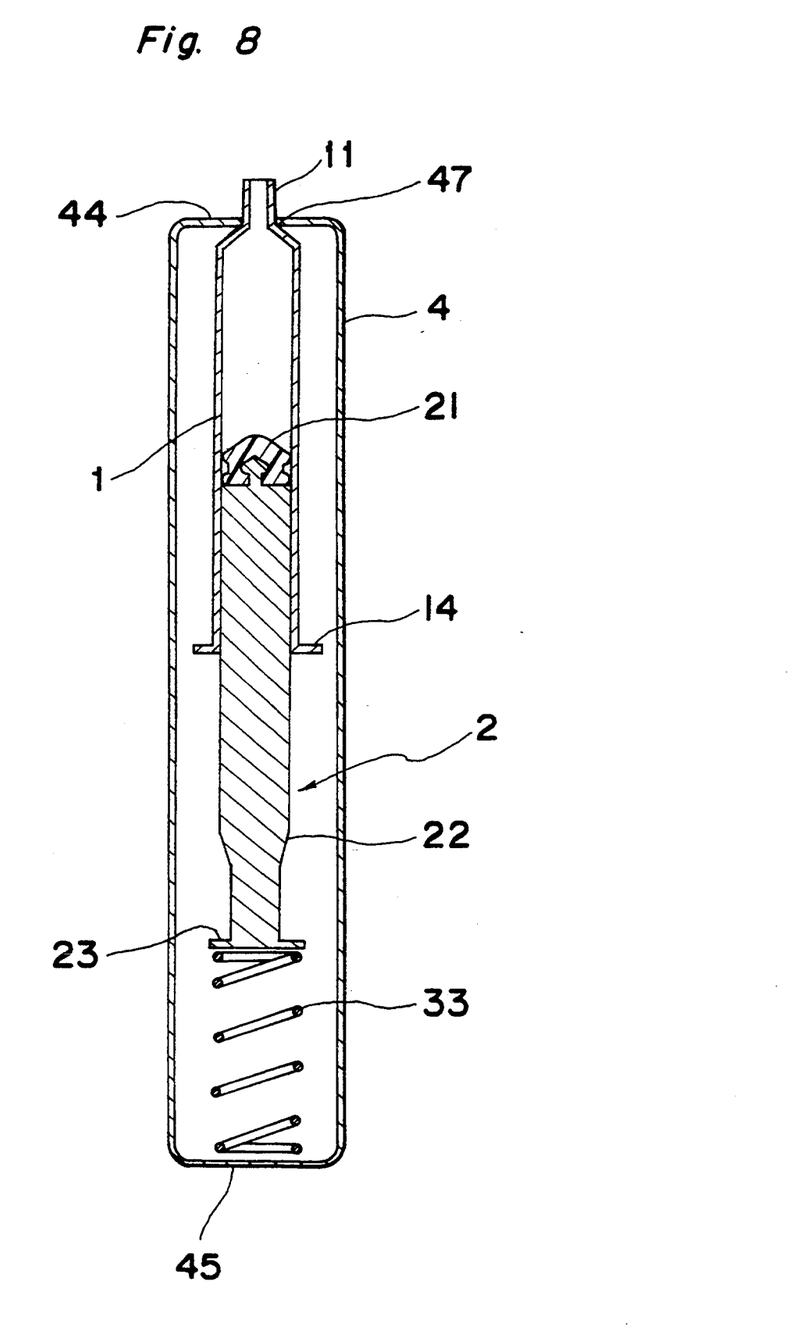
FIG. 8 is a sectional view of a medical solution delivery system illustrating still another embodiment of the present invention.

FIGS. 7 and 8 show an embodiment of a medical solution delivery system employing a coil spring as a source of motive power for returning a displaced plunger to its original position. In the embodiment of FIG. 7, a coil spring 33 is arranged around the syringe and fixed at one end 334 thereof to a rib formed in an inside wall of the capsule 3 on the front side of the capsule 4. The opposite end of the coil spring 33 is fixed to the rear end of the plunger 2 by a suitable fixing means. The opposite end of the spring 33 may be fixed to a disk similar to that used in the embodiment of FIG. 6 as occasion demands.

The embodiment of FIG. 8 has a structure similar to that of the medical solution delivery system of FIG. 7 except that a coil spring 33 is arranged between the flange 22 of the plunger 2 and the rear end wall 45 of the capsule 4.

If the madulus or tensile stress of the rubber spring or coil spring, such as the embodiments of FIG. 6 or FIG. 7, is used for the plunger-driving means 3, it is preferred to minimize the difference between initial and final forces applied to the plunger as much as possible. It is therefore preferred to lengthen the stroke of the rubber spring wire or coil spring as much as possible. This may be done by fixing the front end of the spring to the inside of the front end wall 44 of the capsule 4.

As will be understood from the above, the medical solution delivery system of the present invention is simple in structure and small in the number of components. Thus, it is possible to provide inexpensive medical solution delivery systems. Also, the system is free from elution of chemical substances as the container is of glass or a polyolefine resin. By employing the constant force spring, it is possible to provide a medical solution delivery system capable of injecting a medical solution accurately at a well-controlled flow rate. Further, it is possible to inject the medical solution into the patient safely and certainly since the plunger is housed in the capsule along with the container and the plunger-driving means to prevent them from external influences such as, for example, pressures caused by movement of the body of the patient.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A medical solution delivery system comprising:
   a syringe composed of a cylindrical container and a plunger slidable arranged therein, said container having a narrow part forming a port for a medical solution;
   plunger-driving means of a constant force for forcing the plunger toward the port of the container to deliver a medical solution in the cylindrical container;
   a capsule having a chamber for holding the syringe and the plunger-driving means therein; and
   a flexible connecting tube connectable to the narrow part of said container and provided with flow control means arranged therein to control a flow rate of the medical solution delivered from the syringe;
   said capsule being a cylindrical member having a hole formed at one end thereof so that the narrow part of said container is protruded from the capsule therethrough, said capsule being composed of a capsule body and a covering member removably fitted in the capsule body, said capsule body being provided with an L-shaped slit which extends from a middle part thereof along the barrel of the capsule body to the rear part and then circumferentially extends therefrom to form a short arm portion with a cut.

2. The medical solution delivery system claimed in claim 1, wherein said plunger-driving means comprises a constant force spring wound around a drum, said constant force spring being fixed at one end thereof to the front end of the capsule and being adapted to be in contact with the rear end of the plunger at the opposite wound part thereof.

3. The medical solution delivery system claimed in claim 1, wherein said plunger-driving means comprises a constant force spring wound around a drum, said constant force spring being fixed at one end thereof to the container and being adapted to be in contact with the rear end of the plunger at the opposite wound part thereof.

4. The medical solution delivery system claimed in claim 1, wherein the plunger-driving means is a rubber spring formed in a wire, the rubber spring being fixed at one end thereof to the front side of the capsule and at the opposite end to a disk-like member adapted to be brought into contact with the rear end of the plunger.

5. The medical solution delivery system claimed in claim 1, wherein the plunger-driving means is a coil spring.

6. The medical solution delivery system claimed in claim 5, wherein said coil spring is fixed at one end thereof to the front side of the capsule and at the opposite end to a member adapted to be brought into contact with the rear end of the plunger.

7. The medical solution delivery system claimed in claim 5, wherein said coil spring is arranged between a rear end of the capsule and a rear end of the plunger.

* * * * *